(12) United States Patent
Chuang

(10) Patent No.: US 7,034,070 B2
(45) Date of Patent: Apr. 25, 2006

(54) ARYLALKYL AMINOFUNCTIONAL SILANES FOR EPOXY LAMINATES

(76) Inventor: Vincent Chuang, 11/F-2 #374 Wen-Hwa, 2nd Rd. Sec. 1, Lin-kuo 244 (TW)

( * ) Notice: Subject to any disclaimer, the term of this patent is extended or adjusted under 35 U.S.C. 154(b) by 132 days.

(21) Appl. No.: 10/670,132

(22) Filed: Sep. 24, 2003

(65) Prior Publication Data

US 2004/0110955 A1 Jun. 10, 2004

Related U.S. Application Data

(60) Provisional application No. 60/414,689, filed on Sep. 27, 2002.

(51) Int. Cl.
*C08L 31/02* (2006.01)
*B05D 3/02* (2006.01)

(52) U.S. Cl. .............. 524/262; 524/265; 427/387; 428/447; 525/477

(58) Field of Classification Search ............ 524/262, 524/265; 427/387; 428/447; 525/477
See application file for complete search history.

(56) References Cited

U.S. PATENT DOCUMENTS 3,819,675 A  6/1974  Plueddemann et al.

4,996,257 A  *  2/1991  Saito et al. ............ 524/262

FOREIGN PATENT DOCUMENTS

DE  3912878  * 11/1989
JP  8325439  * 12/1996

* cited by examiner

*Primary Examiner*—D. Margaret Seaman
(74) *Attorney, Agent, or Firm*—Knobbe, Martens, Olson & Bear LLP

(57) ABSTRACT

Epoxy laminates with outstanding strength were obtained from glass fabrics finished with certain non-styryl arylalkyl aminofunctional alkoxysilane compounds having the formula:

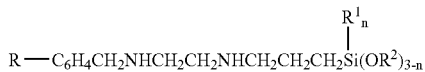

and HCl salts thereof, wherein R is an alkyl group having 1 to 6 carbon atoms; $R^1$ is an alkyl group having 1 to 6 carbon atoms; $R^2$ may be the same or different and are independently selected from alkyl groups having 1 to 6 carbon atoms; and n has a value of 0 or 1, wherein the compounds are prepared using readily available starting materials without the need for styrenic double bond.

21 Claims, No Drawings

ARYLALKYL AMINOFUNCTIONAL SILANES FOR EPOXY LAMINATES

RELATED APPLICATION INFORMATION

This application claims priority under U.S.C. § 119 (e) to U.S. Provisional Application Ser. No. 60/414,689, filed Sep. 27, 2002.

BACKGROUND OF THE INVENTION

1. Field of the Invention

This invention relates to a group of aminofunctional silane coupling agents which find uses as finishes for glass fabrics in the preparation for epoxy lamination composites, e.g. for printed circuit boards (PCB), with better performance than the previously known compounds. In particular, the present invention relates to the synthesis and use of certain arylalkyl aminofunctional silanes, which can be prepared using lower cost, more readily available non-styryl raw materials than that currently used.

2. Description of the Related Art

In fiberglass-reinforced plastics manufacturing, organofunctional alkoxysilanes (commonly referred to as 'coupling agents') are applied to glass fabrics to improve the glass/matrix interface bonding strength and at the same time to prevent penetration of moisture into the interface. Of particular interest to PCB industry which employs epoxy laminates, aminosilanes derived from chloromethylated arylenes, such as Z-6032 and Z-6224 of Dow Coming, A-1128 of OSi (now part of Crompton), are most commonly used. It is well known in the art that in the making of fiberglass reinforced epoxy laminates a process comprising: (1) treatment of glass fabrics with silane solution, (2) impregnation with epoxy resin, and (3) curing at an elevated temperature is involved. In the first step, silane solution in aqueous system is prepared and deemed most desirable for glass-fiber-finishing operations both from the standpoint of cost and safety because of non-flammability. U.S. Pat. No. 3,819,675 discloses a wide variety of cationic unsaturated aminofunctional silane coupling agents for composite applications. One particular composition that has attained remarkable commercial success is styryl aminofunctional silane having the formula:

in applications covering a wide range of polymeric composites. As such, it has gained a status of 'universal' coupling agent, i.e. one that can be used equally well for bonding organic polymers (including polyolefins, unsaturated polyesters, phenolics, epoxy resins, etc.) to inorganic materials. Most unsettling, however, is the question whether the styryl double bond in silane is needed for non-vinylic polymers such as epoxy resins but nevertheless, Z-6032 and its low HCl form Z-6224 have commended a predominant position in epoxy laminates applications for the last three decades, despite the high price. The high price is due to its raw material chloromethyl styrene, $CH_2=CHC_6H_4CH_2Cl$, which is available only from very few sources due to high costs associated with difficulty in manufacturing and product instability, which requires cooling during transportation and storage to prevent polymerization. A-1128 having the formula $C_6H_5CH_2NH(CH_2)_2NH(CH_2)_3Si(OCH_3)_3 \cdot HCl$ derived from a simple chloromethylated arene, benzyl chloride, is a lower cost product but represents a much smaller market presence because of the disadvantage in exhibiting weaker water resistance. Finding a viable alternative product thus becomes imperative.

SUMMARY OF THE INVENTION

In accordance with one embodiment, there is provided aryl aminofunctional silane compounds according to the following formula:

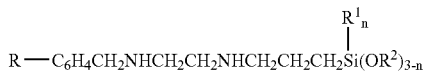

and/or salts thereof, wherein R is an alkyl group having 1 to 6 carbon atoms; $R^1$ is an alkyl group having 1 to 6 carbon atoms; $R^2$ may be the same or different and are independently selected from alkyl groups having 1 to 6 carbon atoms; and n has a value of 0 or 1. Preferred salts include, but are not limited to, HCl salts. In certain preferred embodiments, R is methyl or ethyl, $R^1$ is methyl, and $R^2$ are all methyl or ethyl.

In accordance with a further embodiment, there are provided glass fabric substrates coated with compounds according to the formula above.

DETAILED DESCRIPTION OF THE PREFERRED EMBODIMENT

It has been recognized that, as coupling agents, silane finishes on glass function by having silanol groups bonded to the glass surface and an organofunctional group forming chemical bonds readily with the resin binder. For an effective grafting of silane onto fiberglass surface to take place, it preferably goes through two steps. Alkoxysilane is first hydrolyzed in a bath to form more water-soluble silanol for dipped glass fabrics to pick up. This is then followed by condensation reaction of silanols on the glass surface to complete siloxane bonding. The solution preferably remains soluble in the aqueous system (as indicated by the solution clarity) for as long as the bath content lasts in a production bath. A solution bath life of about 2 days or longer is preferred for practical purposes. In the meantime, during hydrolysis, condensation of silanols takes place concurrently to form water-insoluble siloxane, which is generally ineffective for coupling action. Therefore, preparation of silane solution is preferably conducted under conditions that favor hydrolysis over condensation, typically at ambient temperatures and acidic pH of about 4–5 to minimize premature siloxane formation.

While water solubility is an important characteristic of coupling agents according to preferred embodiments, water resistance of the resultant composite is perhaps even more important. There are many aminofunctional silanes that meet water solubility and solution stability preferences, but the resultant siloxanes are inferior in water resistance. See, for example, A-1100, A-1120 as shown in Modem Plastics, 1962, p. 135. A good coupling agent according to preferred embodiments, therefore, should strike a good—but difficult—balance between hydrophilicity (for hydrolysis) and hydrophobicity (of the resultant siloxane to repel moisture) in the laminates made thereof.

A group of arylalkyl aminofunctional silanes with improved water resistance are found in accordance with preferred embodiments of this invention using more affordable, lower cost chloromethylated arylenes with selected alkyl substitutions. Preferred compounds include aryl aminofunctional silane compounds according to the following formula:

and its salts, wherein R is an alkyl group having 1 to 6 carbon atoms; $R^1$ is an alkyl group having 1 to 6 carbon atoms; $R^2$ may be the same or different and are independently selected from alkyl groups having 1 to 6 carbon atoms; and n has a value of 0 or 1. The term "alkyl group" as used herein is a branched or unbranched chain having from 1 to 6 carbon atoms. Preferred salts include, but are not limited to, HCl salts.

The compounds of above composition produced by a process according to preferred embodiments perform substantially the same and, in some respects, provide better results than the previously known products, without the need for high cost styryl raw materials. The products are also more stable, being non-vinylic, and thus easier to handle. The superiority of the silane composition according to preferred embodiments will become apparent as shown in Example 4 below for water solution stability, Example 5 for bonding strength, and in Example 6 for boiling water resistance using the industrial standard test (121° C., +1 atm) and the more stringent pressure cooker test (132° C., +2 atm), both of which were followed by the 500° F. solder bath test. The results of the testing unravels the long lingering question of the styryl double bond mystery, that is, with proper alkyl substitutions on the arylenes, non-styrenic silanes can perform just as well for epoxy resin lamination, which was not heretofore realized.

Quite unexpected also is the higher hydrophobicity in some preferred embodiments that requires longer hydrolysis time than the benchmark product currently in use (see Example 4) yet still maintains longer solution stability once dissolved in water, a seemingly incompatible but most desirable feature in the preparation and handling of aqueous silane solution for glass-fiber-finishing operation.

Compounds according to preferred embodiments may be made by a process involving reacting a compound according to the formula below:

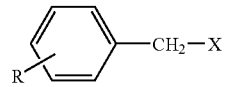

wherein X is a leaving group, preferably a halide such as chloride, with the appropriate aminosilane compound. The reaction preferably proceeds by adding a solution comprising the benzyl compound in a compatible solvent slowly, such as dropwise, to the aminosilane under heating, including reflux.

The compositions in the following examples, which are as structurally illustrated and further characterized with respect to physical properties, are merely illustrative of the invention and not to be regarded as limiting.

EXAMPLE 1

Preparation of $CH_3CH_2C_6H_4CH_2NH(CH_2)_2NH(CH_2)_3Si(OCH_3)_3 \cdot HCl$ (I)

The preparation of the compound according to formula (I), above, proceeds as follows:

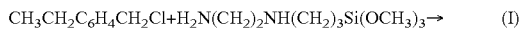

Into a 2-liter 3-necked round bottom flask equipped with addition funnel, reflux condenser, thermometer, and stirrer, are charged 226 g (1.02 moles) of commercially available 2-aminoethyl(3-aminopropyl)trimethoxysilane (A-1120 from OSi) and heated to 60° C. Over a period of 1 hour 156 grams (1.0 mole) of ethylbenzyl chloride in 570 grams anhydrous methanol are added drop-wise to the pot with stirring while maintaining gentle reflux (65°–70° C.) with occasional heating. Stirring under reflux for additional 2 and half hours completes the alkylation of amino nitrogen of the silane with the accompanying formation of near theoretical (1.05 moles/kg) chloride ion by analysis of a reconstituted 40 wt-% methanol solution. The starting material ethylbenzyl chloride as used consisted of para- and ortho-isomers in about 70:30 ratio, which was consistent with NMR spectroscopy data. No isolation of the product was attempted due to highly hygroscopic nature of the amine salt product and hydrolysis sensitive trimethoxysilane ester group. The product obtained (950 grams) has the physical properties as follows: Specific gravity at 25° C., 0.901; Refractive index $n_D^{25}$, 1.396; Cl⁻, 3.70%; ¹H NMR (CD$_3$OD, TMS) δ=0.6 (2H, br m), 1.15(3H, t, J=7.26 Hz), 1.6(2H, br m), 2.55(2H, q, J=7.55 Hz), 2.8(6H, m), 3.3(9H, s), 3.9(2H, s), 7.16(4H, m) (some signals were hidden in broad peak of CH$_3$OH and CHOH (solvent) which appeared at δ=3.4 and 5.0 ppm respectively).

EXAMPLE 2

Preparation of $CH_3CH_2C_6H_4CH_2NH(CH_2)_2NH(CH_2)_3Si(OCH_3)_3$ (II)

A low chloride version was obtained by neutralization with alcoholic NaOH. The preparation of the compound according to formula (II), above, proceeds as follows:

The product obtained in Example 1 (940 grams of I) is neutralized by adding gradually under vigorous agitation a solution containing 40 grams of NaOH dissolved in 150 grams of methanol, and the NaCl precipitate formed is removed by filtration to obtain a clear solution of the product (1022 grams of II), which has: Specific gravity at 25° C., 0.879; Refractive Index at 25° C., 1.389; Cl⁻, 0.3%; ¹H NMR (CD$_3$OD, TMS) δ=0.6(2H, br s), 1.15(3H, br t), 1.6(2H, br m), 2.5 (8H, br overlapped m), 3.3(9H, s), 7.1(4H, m) (some signals were hidden in broad peak of CH$_3$OH and CHOH (solvent) which appeared at δ=3.4 and 5.0 ppm respectively).

EXAMPLE 3

Preparation of $CH_3CH_2C_6H_4CH_2NH(CH_2)_2NH(CH_2)_3SiCH_3(OCH_3)_2 \cdot HCl$ (III)

The preparation of the compound according to formula (III), above, proceeds as follows:

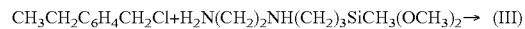

The procedure of Example 1 was followed using 156 grams (1.0 mole) of ethylbenzyl chloride in 550 grams of anhydrous methanol and 210 g (1.02 moles) of 2-aminoethyl (3-aminopropyl)methyldimethoxysilane (KBM 602 from Shin-Etsu) to produce 915 grams of 40 wt-% solution of ethylbenzylated aminoalkylmethyldimethoxysilane hydrochloride that is amber in color and shows the anticipated chloride ion analysis of 1.09 moles/kg with the physical properties as follows: Specific gravity at 20° C., 0.890; Refractive index $n_D^{25}$, 1.4040; Cl⁻, 3.87%; ¹H NMR (CD₃OD, TMS) δ=0.15(3H, s), 0.55(2H, br m), 1.15(3H, t, J=7.26 Hz), 1.6(2H, br m), 2.55(2H, q, J=7.55 Hz), 2.8(6H, m), 3.3(6H, s), 3.9(2H, s), 7.16(4H, m) (some signals were hidden in broad peak of CH₃OH and CHOH (solvent) which appeared at δ=3.4 and 5.0 ppm respectively).

EXAMPLE 4

Water Solubility Test

With stirring, 1.0 gram sample from Example 1 was added gradually to 100 ml of distilled water acidified with 1% glacial acetic acid. The solution was slightly hazy at the beginning but turned clear after 45 min. while the commercial product Z-6032 (Dow Coming) under similar conditions turned clear in 20 min. The solution stayed clear for more than two weeks at ambient temperatures while that from Z-6032 turned hazy in less than 1 week.

EXAMPLE 5

Bonding Strenght

A. Preparation of Silane Finish Solution

An aqueous silane solution was prepared by adding, in the sequence, 10 g of acetic acid and 6.7 g of silane product obtained from Example 1 (which contains 40 percent active silane), into 1000 ml of distilled water to provide 0.67% (nominal) or 0.27% (actual) concentration of the coupling agent solution. The solution was vigorously stirred at an ambient temperature for 1 hour to obtain a clear silane finish solution.

B. Treatment of Glass Fabrics

Type 7628 heat-cleaned glass cloth was dipped into the silane finish solution prepared in 5A at an ambient temperature for 2.5 min. The silane treated glass fabric was passed through a set of rollers to squeeze out excess silane solution then dried at 115° C. for 30 min. The dry treated 7628 glass fabrics had silane pick-up of 0.08 wt-%, and for thinner gauge 1080 fabrics pick-up of 0.12%. The glass fabric was cut into 5×25 cm² specimens and subjected to tensile strength test. Tensile testing was carried out using Instron overhead speed of 10 cm/min. The results are shown in Table 1. The columns headed "Tensile Strength" is the tensile strength at break (kg/5 cm) and the columns headed RTS % is the relative tensile strength with 128.7 kg/5 cm (0.67% Z-6224) taken as 100.

EXAMPLE 6

Water Resistance of Multi Layer Laminate by FR-4 Epoxy Resin

A. Preparation of Epoxy Varnish Solution

| Formulation: | Epoxy resin | Araldite 8011A-80 | 143 parts |
|---|---|---|---|
| | Hardener | Dicyandiamide | 4 parts |
| | Cure agent | Methyl imidazoline | 0.2 parts |
| | Solvent | Dimethyl formamide | |

B. Preparation of Laminate

Four-ply laminates: Strips of Type 7628 glass fabrics treated with silane finish in 5B-1 above were impregnated with the above varnish (6A); pre-cure at 150° C. for 5 min., press-cure with gradual increase of temperature to 190° C. and pressure to 35 kg/cm² in 15 min. and held for 2 hours.

C. Boiling Water Resistance Test (I). Pressure Cooker:

The conditions for the standard test are a temperature of about 121° C. steam (at a pressure of 1 atm) and a time of one hour.

The conditions for the accentuated test were a temperature of about 132° C. steam (at a pressure of 2 atm.) and a time of either one hour or two hours.

The laminate specimens were immersed in the pressure cooker under boiling conditions as specified above for one or two hours (II). Solder Bath:

After the pressure cooker exposure above, each specimen was immersed into a solder bath maintained at 500±10° F. (260±5° C.) according to IPC-TM-650 Test Methods for a time of about 20 seconds. The results are shown in Table 2 for samples using the finish of Example 1 prepared according to the procedure of Example 5A.

TABLE 2

Boiling Water Resistance of Multi Layer Laminate by FR-4 Epoxy Resin

| Sample No. | Standard | Accentuated (1 hour) | Accentuated (2 hours) |
|---|---|---|---|
| 1 | No blister | No blister | No blister |
| 2 | No blister | No blister | No blister |
| 3 | No blister | No blister | No blister |

TABLE 1

Tensile Strength of Silane-treated Glass Fabrics 7628

| | Z-6224 (40% solids) | | Example 1 (40% solids) | | Example 3 (40% solids) | | No Silane | |
|---|---|---|---|---|---|---|---|---|
| Silane Conc. | Tensile Strength | RTS % | Tensile Strength | RTS % | Tensile Strength | RTS % | Tensile Strength | RTS % |
| 0.40% | 110.4 | 85.8 | 122.9 | 95.5 | — | — | — | — |
| 0.50% | 122.2 | 94.9 | — | — | — | — | — | — |
| 0.67% | 128.7 | 100 | 140.4 | 109 | 140 | 109 | — | — |
| 1.00% | 131.6 | 102 | 139.1 | 108 | — | — | — | — |
| 0.00% | — | — | — | — | — | — | 54.3 | 42 |

TABLE 2-continued

Boiling Water Resistance of
Multi Layer Laminate by FR-4 Epoxy Resin

| Sample No. | Standard | Accentuated (1 hour) | Accentuated (2 hours) |
|---|---|---|---|
| 4 | No blister | No blister | No blister |
| 5 | No blister | No blister | Blister |

The various methods and techniques described above provide a number of ways to carry out the invention. Of course, it is to be understood that not necessarily all objectives or advantages described may be achieved in accordance with any particular embodiment described herein. Thus, for example, those skilled in the art will recognize that the methods may be performed in a manner that achieves or optimizes one advantage or group of advantages as taught herein without necessarily achieving other objectives or advantages as may be taught or suggested herein.

Furthermore, the skilled artisan will recognize the interchangeability of various features from different embodiments. Similarly, the various features and steps discussed above, as well as other known equivalents for each such feature or step, can be mixed and matched by one of ordinary skill in this art to perform methods in accordance with principles described herein.

Although the invention has been disclosed in the context of certain embodiments and examples, it will be understood by those skilled in the art that the invention extends beyond the specifically disclosed embodiments to other alternative embodiments and/or uses and obvious modifications and equivalents thereof. Accordingly, the invention is not intended to be limited by the specific disclosures of preferred embodiments herein, but instead by reference to claims attached hereto.

What is claimed is:

1. An aryl aminofunctional silane compound having the formula:

$$R\text{---}C_6H_4CH_2NHCH_2CH_2NHCH_2CH_2CH_2Si(OR^2)_{3-n}\overset{R^1_n}{|}$$

and/or HCl salts thereof
wherein R is an alkyl group having 2 to 6 carbon atoms; $R^1$ is an alkyl group having 1 to 6 carbon atoms; $R^2$ may be the same or different and are independently selected from alkyl groups having 1 to 6 carbon atoms; and n has a value of 0.

2. An aryl aminofunctional silane compound according to claim 1 wherein $R=CH_3$ and $R^2=C_2H_5$, and n=0

and the HCl salt thereof, wherein methyl group is ortho-, meta-, or para-substituted or mixtures thereof.

3. An aryl aminofunctional silane compound according to claim 1 wherein $R=C_2H_5$, $R^2=CH_3$, and n=0

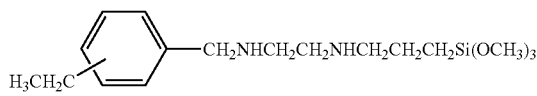

and the HCl salt thereof, wherein ethyl group is ortho-, meta-, or para-substituted or mixtures thereof.

4. An aryl aminofunctional silane compound according to claim 1 wherein $R=C_2H_5$, $R^2=C_2H_5$, and n=0

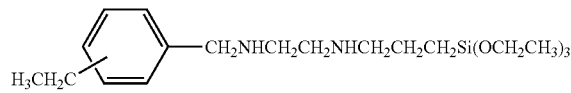

and the HCl salt thereof, wherein ethyl group is ortho-, meta-, or para-substituted or mixtures thereof.

5. An aryl aminofunctional silane compound according to claim 1 wherein $R=C_3H_7$, $R^2=CH_3$, and n=0

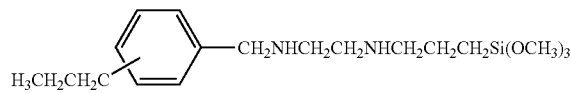

and the HCl salt thereof, wherein propyl group is ortho-, meta-, or para-substituted or mixtures thereof.

6. An aryl aminofunctional silane compound according to claim 1 wherein $R=C_3H_7$, $R^2=C_2H_5$, and n=0

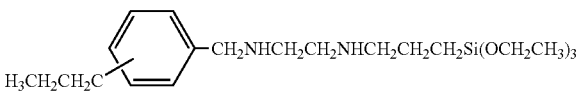

and the HCl salt thereof, wherein propyl group is ortho-, meta-, or para-substituted or mixtures thereof.

7. An aryl aminofunctional silane compound having the formula:

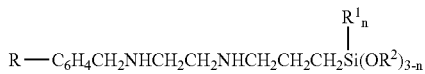

and/or HCl salts thereof
wherein R is an alkyl group having 1 to 6 carbon atoms; $R^1$ is an alkyl group having 1 to 6 carbon atoms; $R^2$ may be the same or different and are independently selected from alkyl groups having 1 to 6 carbon atoms; and n has a value of 1.

8. A water-resistant substrate, comprising a glass fabric coated with at least one compound according to claim 7.

9. A water-resistant substrate according to claim 8, wherein the coating amount of the compound is about 0.05 to 0.2% by weight based on the weight of glass fabric.

10. A water-resistant substrate according to claim 8, wherein the coating amount of the compound is about 0.065 to 0.15% by weight based on the weight of glass fabric.

11. A method of preparing a substrate, comprising:
applying at least one compound according to claim 7 to a glass fabric to form a coated glass fabric; and
applying the coated fabric to an epoxy laminate thereby reinforcing the laminate.

12. An aryl aminofunctional silane compound according to claim 7 wherein $R=CH_3$, $R^1=CH_3$, $R^2=CH_3$, and n=1

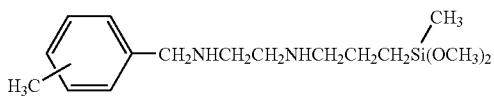

and the HCl salt thereof, wherein methyl group is ortho-, meta-, or para-substituted or mixtures thereof.

13. An aryl aminofunctional silane compound according to claim 7 wherein R=CH$_3$, R$^1$=CH$_3$, R$^2$=C$_2$H$_5$, and n=1

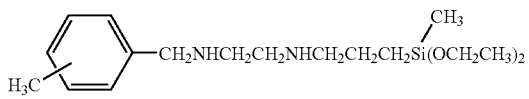

and the HCl salt thereof, wherein methyl group is ortho-, meta-, or para-substituted or mixtures thereof.

14. An aryl aminofunctional silane compound according to claim 7 wherein R=C$_2$H$_5$, R$^1$=CH$_3$, R$^2$=CH$_3$, and n=1

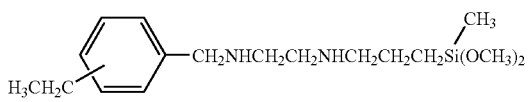

and the HCl salt thereof, wherein ethyl group is ortho-, meta-, or para-substituted or mixtures thereof.

15. An aryl aminofunctional silane compound according to claim 7 wherein R=C$_2$H$_5$, R$^1$=CH$_3$, R$^2$=C$_2$H$_5$, and n=1

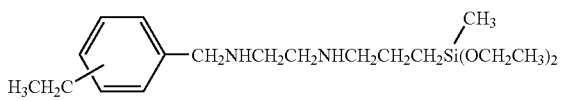

and the HCl salt thereof, wherein ethyl group is ortho-, meta-, or para-substituted or mixtures thereof.

16. An aryl aminofunctional silane compound according to claim 7 wherein R=C$_3$H$_7$, R$^1$=CH$_3$, R$^2$=CH$_3$, and n=1

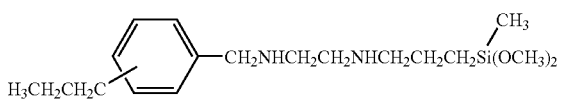

and the HCl salt thereof, wherein propyl group is ortho-, meta-, or para-substituted or mixtures thereof.

17. An aryl aminofunctional silane compound according to claim 7 wherein R=C$_3$H$_7$, R$^1$=CH$_3$, R$^2$=C$_2$H$_5$, and n=1

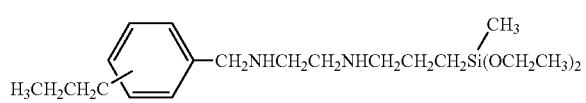

and the HCl salt thereof, wherein propyl group is ortho-, meta-, or para-substituted or mixtures thereof.

18. A water-resistant substrate, comprising a glass fabric coated with at least one compound according to claim 1.

19. A water-resistant substrate according to claim 18, wherein the coating amount of the compound is about 0.05 to 0.2% by weight based on the weight of glass fabric.

20. A water-resistant substrate according to claim 18, wherein the coating amount of the compound is about 0.065 to 0.15% by weight based on the weight of glass fabric.

21. A method of preparing a substrate, comprising:
applying at least one compound according to claim 1 to a glass fabric to form a coated glass fabric; and
applying the coated fabric to an epoxy laminate thereby reinforcing the laminate.

* * * * *